United States Patent [19]

Iversen et al.

[11] Patent Number: 5,643,890
[45] Date of Patent: Jul. 1, 1997

[54] SYNTHETIC OLIGONUCLEOTIDES WHICH MIMIC TELOMERIC SEQUENCES FOR USE IN TREATMENT OF CANCER AND OTHER DISEASES

[75] Inventors: Patrick L. Iversen, Ralston; John E. Mata, Omaha, both of Nebr.

[73] Assignee: The Board of Regents of the University of Nebraska, Lincoln, Nebr.

[21] Appl. No.: 381,097

[22] Filed: Jan. 31, 1995

[51] Int. Cl.$^6$ .............................. A61K 48/00; C12N 5/10; C07H 21/04
[52] U.S. Cl. ...................... 514/44; 424/93.21; 435/375; 536/23.1
[58] Field of Search ........................ 435/240.2; 514/44; 536/23.1, 24.5; 424/93.21

[56] References Cited

U.S. PATENT DOCUMENTS 5,264,423  11/1993  Cohen et al. ........................ 514/44

FOREIGN PATENT DOCUMENTS

WO93/23572  11/1993  WIPO .

OTHER PUBLICATIONS

Han, Jian et al., "Selection of Antisense Oligonucleotides On The Basis Of Genomic Frequency Of The Target Sequence", 1994 *Antisense Research And Development*, 4:53–65.
Zahler, Alan et al., "Inhibition Of Telomerase By G–Quartet DNA Structures", 1991, *Nature*, vol. 350, p. 718–720.
Blackburn, Elizabeth, "Structure And Function Of Telomeres", 1991, *Nature*, vol. 350, p. 569–5973.
Biessmann, Harold et al., "Genetics And Molecular Biology Of Telomeres", 1992, *Advances In Genetics*, vol. 30, pp. 185–249.
Strahl, Catherine et al., "The Effects Of Nucleoside Analogs On Telomerase And Telomeres In Tetrahymena", 1994, *Nucleic Acids Research*, Vo. 22, No. 6, pp. 893–900.
Blackburn, Elizabeth, "Telomeres", 1991, *TIBS*.
"Chromosome Ends Catch Fire", Sep. 1994, *Science*, vol. 265, p. 16561658.
Romero, Daniel et al., 1991, "A Conserved Secondary Structure For Telomerase RNA", *Cell*, vol. 67, 343–353.
Counter, Christopher et al., 1992, "Telomere Shortening Associated With Chromosome Instability Is Arrested In Immortal Cells Which Express Telomerase Activity", 1992, *The EMBO Journal*, vol. 11 No. 5, pp. 1921–1929.
Greider, 1990, Telomeres, Telomerase And Senescence, *BioEssays*, vol. 12, No. 8, pp. 363–369.
Prowse, 1993, Identification Of A Nonprocessive Telomerase Activity From Mouse Cells, *Proc. Natl. Acad. Sci. USA*, vol. 90, pp. 1493–1497, Feb. 1993.
Kim, 1994, Specific Association Of Human Telomerase Activity With Immortal Cells And Cancer, *Science*, vol. 266:2011–2014.
Grieder et al., "A Telomeric Sequence in the RNA of Tetrahymena Telomerase Required for Telomere Repeat Synthesis", Nature, vol. 337, pp. 331–337. Jan. 26, 1989.

*Primary Examiner*—George C. Elliott
*Assistant Examiner*—Amy J. Nelson
*Attorney, Agent, or Firm*—Zarley, McKee, Thomte, Voorhees, & Sease

[57] ABSTRACT

A method of inhibiting proliferation of immortal cells or cells that express telomerase is disclosed. The method includes introduction of synthetic oligonucleotides which mimic telomere motifs. Quite surprisingly applicant has demonstrated that a single telomere motif, TTAGGG exhibits greater cellular uptake and higher inhibition of proliferation than longer oligonucleotides, which were previously thought to be necessary to achieve sequence specific interaction with telomerase.

25 Claims, 6 Drawing Sheets

SYNTHETIC OLIGONUCLEOTIDES WHICH MIMIC TELOMERIC SEQUENCES FOR USE IN TREATMENT OF CANCER AND OTHER DISEASES

BACKGROUND OF THE INVENTION

There are an estimated 200 different kinds of cancer, each of which has the common property of uncontrolled growth of neoplastic cells derived from normal tissues. More than 900,000 new cases of cancer are diagnosed annually in the United States and there are 600,000 deaths from cancer each year.

Despite considerable success in the treatment of several specific tumors, the overall survival rate for most cancers has not changed dramatically over the past few years. Surgery in combination with chemotherapy has proved successful in treatment of early localized disease, but the development of clinical metastases, or spread of cancer to distal sites, remains the primary cause of cancer morbidity and mortality. Metastatic disease is incurable with a median survival of 2.2 years from the time of documented metastases.

The major problem in anti-neoplastic therapy is the ability of therapeutic agents to distinguish neoplastic from normal cells. Attempts to distinguish neoplastic from normal cells on the basis of proliferative behavior has proven quite limited. Thus the search has continued for biochemical characteristics of neoplastic cells that are tumor specific rather than proliferation specific. Unfortunately current molecular genetic studies have failed to support the hope that such characteristics are a consistent feature of neoplastic cells. Rather the studies suggest that the neoplastic state can be explained without postulating tumor-specific functions, but merely by the operation of normal proliferation-specific functions at abnormal levels, as the result of changes (often times minimal) in the structure of growth-regulator genes or changes in their number or chromosomal environment. The search for attributes of neoplastic cells which can provide for selective treatment continues.

Current trends and treatments for cancer have included alternative approaches that do not depend on the natural occurrence of such biochemical differences. One alternative strategy entails the artificial creation of differences between normal and neoplastic cells through prophylactic use of gene insertion techniques. In other words the manufacturing of biochemical differences which can be exploited to systematically and specifically target neoplastic cells for destruction. This type of protocol is highly complex, controversial, and unpredictable.

Perhaps the most successful of these protocols includes the transduction of tumor cells with a sequence encoding for the Herpes Simplex I thymidine kinase gene combined with subsequent treatment with an anti-viral agent (such as gancyclovir) to selectively kill tumor cells which express the gene. This type of gene therapy is fraught with controversy and problems and it's development is only in its infancy.

Thus a need exists in the art for a simple anti-neoplastic therapy which takes advantage of naturally occurring biochemical differences between neoplastic and normal cells so that these cells can be selectively targeted and destroyed.

It is an object of the present invention to provide a simple method for inducing cell death and inhibiting the uncontrolled proliferative behavior of cancerous and other cells which represent disease states with uncontrolled growth and replication.

It is another object of the present invention to provide anti-proliferative agents and pharmaceutical compositions for selective destruction of neoplastic cells.

SUMMARY OF THE INVENTION

Normal human somatic cells (e.g. fibroblasts endothelial and epithelial cells) display a replicative capacity of 50–200 population doublings characterized by a cessation in proliferation in spite of the presence of abundant growth factors. This cessation of replication in vitro is referred to as cellular senescence or cellular aging. The replicative life span of cells is inversely proportional to the in vivo age of the donor thus cellular senescence is suggested to play an important role in aging in vivo.

Cellular immortalization (the acquisition of unlimited replicative capacity) may be thought of as an abnormal escape from cellular senescence. Normal human somatic cells have finite replicative potential. In contrast germ line and malignant tumor cells are immortal (have indefinite proliferative potential).

The present invention relates to oligonucleotide strategies which are designed to forestall the capacity of neoplastic cells to uncontrollably proliferate. The strategy specifically targets naturally occurring biochemical agents in neoplastic cells which allow for their escape from cellular senescence and inhibits these agents to cause cell death.

The present invention relates to a method of anti-neoplastic therapy through activity of proliferation inhibitors (oligonucleotides). According to traditional oligonucleotide therapy, a synthetic oligonucleotide of approximately 14 nucleotides, preferably complementary to DNA (antigene) or RNA (antisense), which interferes with the process of transcription or translation of endogenous proteins in cells or in animals is introduced. Quite surprisingly applicants have discovered that oligonucleotides of as little as 6 bases which are designed to mimic or interact with telomere motifs cause significant decreases in immortal cell proliferation.

As used herein the term antisense is intended to encompass all forms of oligonucleotide strategy including antigene, anti-sense, etc. and is intended in no way to imply a particular design of an oligonucleotide or its hybridization to a target.

Antisense oligonucleotides represent potential tools in research and therapy by virtue of their ability to specifically inhibit synthesis of target proteins. A major theoretical advantage of these oligos is their potential specificity for binding to one site in the cell. According to the invention the oligo is introduced to cells by methods which are known to those of skill in the art. See, Iversen, et al., "Anti-Cancer Drug Design", Vol. 6 pp. 531–538 "In Vivo Studies With Phosphorothiotate Oligonucleotides: Pharmacokinetic Prologue"; Iverson P. L. published by McMillan Press. 1991, 6531–6538, incorporated herein by reference. While not wishing to be bound by any theory, it is postulated that hybridization of proteolytic enzyme mRNA with the introduced complementary oligo occurs, effectively blocking translation. The nucleotide sequences of the modified oligos which inhibit synthesis of these enzymes need not be wholly (100%) complementary to be useful in the present invention. As used herein the term "substantially analogous" shall mean an oligo of approximately 80% complementary or homology to the telomere sequence or repeat motif.

Aptamers are synthetic chains of nucleotides that block the disease-causing activity of certain proteins. For example, the thrombin-inhibitor GS522, a synthetic oligonucleotide designed as an anti-coagulant that binds thrombin (Gilead Sciences, Annual Report, 1994 p. 16–17).

In contrast, the present invention employs a single-stranded synthetic oligonucleotide as a telomere motif decoy (TELIGO) which effectively inhibits the telomerase enzyme (a ribonucleoprotein complex). The advantages of such a strategy include fewer competing sites (there are less than approximately 50 endogenous sites in the human genome), inhibition of telomerase activity involves both hybridization of complementary sequences of nucleic acids (antisense) and allosteric binding (aptameric binding) to the ribonucleoprotein complex, the telomere which the TELIGO mimics is identical in all higher vertebrates, hence drug development can utilize animal models, and the ease and cost in purification of a 6-mer is considerably less than a standard antisense oligo.

Traditional limitations of oligonucleotide therapy have been preparation of the oligonucleotide analogue which is substantially resistant to the endo and exonucleases found in the blood and cells of the body. While unmodified oligos have been shown to be effective, several modifications to these oligos have helped alleviate this problem.

Modified or related nucleotides of the present invention can include one or more modifications of the nucleic acid bases, sugar moieties, internucleoside phosphate linkages, or combinations of modifications at these sites. The internucleoside phosphate linkages can be phosphorothioate, phosphoramidate; methylphosphonate, phosphorodithioate and combinations of such similar linkages (to produce mixed backbone modified oligonucleotides). Modifications may be internal or at the end(s) of the oligonucleotide molecule and can include additions to the molecule of the internucleoside phosphate linkages, such as cholesterol, diamine compounds with varying numbers of carbon residues between the amino groups, and terminal ribose, deoxyribose and phosphate modifications which cleave, or crosslink to the opposite chains or to associated enzymes or other proteins which bind to the genome. While oligonucleotides have been shown to be effective without any modifications, these modifications traditionally help shield it from enzymatic degradation within the cell.

Pharmacokinetics of phosphorothioate oligonucleotides have been studied a great deal and have been shown to be favorable for in vivo treatment methods. See "Cellular Uptake In Subcellular Distribution Of Phosphorothioate Oligonucleotides Into Cultured Cells", Antisense Research & Development II: 211–222 (1992). Iversen et al. incorporated herein by reference which demonstrates that phosphorothioate oligonucleotides are taken up into cells within one hour and sequestered into both nuclei and mitochondria of cells in a time-dependent manner. Also incorporated herein by reference is the article "In Vivo Studies With Phosphorothioate Oligonucleotides": Pharmacokinetics Prologue, Iversen, P. Anti Cancer Drug Design (1991), 6531–538. This paper discusses the half-life of phosphorothioate oligonucleotides administered intravenously or intra paritoneally and discloses a biphasic plasma elimination of the oligonucleotide including a distribution half-life of 15–25 minutes and an elimination half-life of 20–40 hours and that repeated in daily injections of oligonucleotide provides steady state concentration in 6–9 days and indicates that phosphorothioate oligos are relatively non-toxic and concludes "pharmacokinetic considerations are not likely to be limiting factors in anti-cancer drug design with phosphorothioate oligonucleotides".

Also incorporated by reference herein are "Iversen et al, Pharmacokinetics of an anti-sense phosphorothioate oligo oxynucleotide against rev and from human immunodeficiency virus Type I in the adult male rat following single injections and continuous infusion", Antisense Research & Development, 4, 43–52 (1994). Again, this article discusses uptake and distribution of phosphorothioate oligonucleotides administered through intravenous injections and subcutaneous infusions. No toxicity was seen and plasma concentration was directly proportional to dose. Oligonucleotide was completely eliminated in urine over 3 days again concluding that phosphorothioate oligonucleotides are promising as therapeutic agents in vivo. Further Agrawal et al. 1991 indicate that phosphorothioate oligonucleotides can achieve potentially therapeutic concentrations (about 0.1–1 µM in at least several tissues of mice, rats and monkeys. Degradation is slow in vivo. Finally incorporated hereby in reference is Bayever et al, Systematic administration of a phosphorothioate oligonucleotide with a sequence complementary to p53 for acute myelogenous leukemia and myelodysplastic syndrome: initial results of a Phase I trial. Antisense Research and Development 3:383–390 (1993). This paper discusses pharmacokinetics of phosphorothioate oligonucleotides administered to human patients. Oligonucleotide was administered via continuous intravenous infusion and no major toxicity was seen for a dose of 0.05 mg/kg/hr. The article concludes that safety and favorable pharmacokinetics support the further investigations of phosphorothioate oligonucleotides as potential gene specific therapeutic agents in humans.

Any of the known methods for oligonucleotide synthesis can be used to prepare the oligonucleotides. They are most conveniently prepared using any of the commercially available, automated nucleic acid synthesizers, such as Applied Biosystems, Inc., DNA synthesizer (Model 380B), According to manufacturers protocols using phosphoroamidite chemistry. Phosphorothioate oligonucleotides were synthesized and purified according to the methods described in Stec and Zon J. Chromatography, 326:263–280 and in Applied Biosystems, DNA Synthesizer, User Bulletin, Models 380A-380B-381A-391-EP, December 1989.

As used herein the term "therapeutically effective amount" of an oligonucleotide is a well recognized phrase. Those skilled in the medical arts will readily appreciate that the doses and schedules of oligonucleotide will vary depending on the age, health, sex, size and weight of the patient rather than administration, etc. These parameters can be determined for each system by well-established procedures and analysis e.g., in phase I, II and III clinical trials.

For human in vivo use preferred dosage of the oligonucleotides of the present invention is that which is necessary to attain a concentration in blood of from about 0.01 to about 1 µM. This concentration can be achieved in a variety of ways. Doses of between about 0.05 and about 0.25 mg/kg/hr by continuous IV infusion have been found to be acceptable. Greater or lesser amounts of oligonucleotide may be administered as required.

For such administration the oligonucleotide or conjugate thereof can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like. Traditionally IV therapy is preferred.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, drageemaking, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, include for example, sodium carboxymethyl cellulose, sorbitol and/or dextran, optionally the suspension may also contain stabilizers.

In addition to administration with conventional carriers, active ingredients may be administered by a variety of specialized delivery drug techniques which are known to those of skill in the art.

DETAILED DESCRIPTION OF THE INVENTION

A telomere is a specialized structure at the 3' end of chromosomes in most living organisms. They function in chromosome protection, positioning, and replication. Generally, telomeres consist of hundreds to thousands of tandem repeats of a telomere motif sequence and associated proteins. In humans and other mammals this motif is 5'-d (TTAGGG)-3'. Sequences specific to other species such as yeasts, plants and ciliates may be found in Greider, Carrol, "Telomeres Telomerase and Senescence", Bio Assays, Vol. 12, No. 8, August 1990, pp. 363–369, incorporated herein by reference.

In humans the average telomere length of sperm DNA is 15 kb. As an organism ages, however, its telomere length becomes shorter. This phenomenon which has caused telomeres to become characterized as a mitotic clock and thus responsible for the limited proliferative capacity of somatic cells. It has been demonstrated that chromosomes lose about 50–200 nucleotides of telomeric sequence per cell division.

This loss of sequence from the 3' end of DNA is primarily due to the activity of DNA polymerase and its replication of DNA prior to cell division. DNA polymerase requires a primer for DNA replication and proceeds only in the 5' to 3' direction.

Figure 1A:
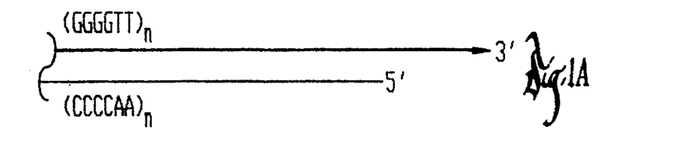
FIGS. 1A–1C is a schematic illustrating denovo telomere elongation. 1A The structure of the tetrahymena telomere is shown with its overhang. 1B Denovo elongation of the TTGGGG SEQ ID NO: 1 strand in the 5' to 3' direction results in telomere elongation. 1C the CCCCAA SEQ ID NO: 2 strand can be filled in by conventional lagging strand synthesis.
Figure 1B:
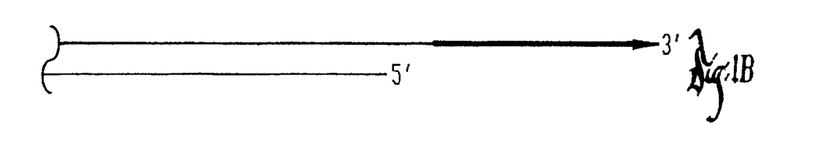
Figure 1C:
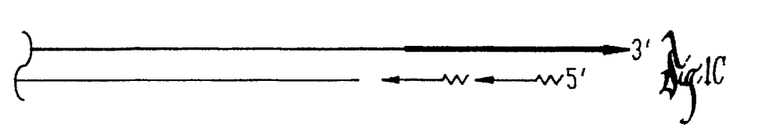

The molecular end of the DNA molecule with the 3' end leading strand proceeds to the end of the DNA molecule, while lagging strand replication must utilize RNA primers and Okazaki fragments synthesis. Removal of the RNA primers Okazaki fragment ligation leaves a region at one end of each daughter molecule unreplicated. With no mechanism to fill the gap the chromosome gets shorter with each round of replication. After numerous rounds of replication a great amount of DNA could be lost from chromosome ends. Telomeres thus provide a measure by which a cell can gauge its divisons. A sufficiently short telomere is postulated to be the signal for replicative senescence, or apoptosis in normal cells. FIG. 1 shows denovo telomere elongation.

In stark contrast, virtually all immortal cells and stem cells examined to date show no net loss of telomere length or sequence with cell division, suggesting that maintenance of telomeres is required for cells to escape from replicative senescence and proliferate indefinitely. The enzyme capable of synthesizing telemere sequence is telomerase.

Telomerase is a ribonucleoprotein that synthesizes telomeric DNA onto 3' chromosome ends using a segment of its RNA component as a template It can perform denovo synthesis of the telomeric repeat (5'-d(TTAGGG)-3') SEQ ID NO: 3 for humans and other mammals). This function thus compensates for the inability of DNA polymerase to completely replicate the ends of linear DNA molecules. Telomerase could also function to protect ends of linear chromosomes from degradation, recombination and ligation to other chromosome ends. Telomerase activity has been identified in germ line cells and tumor cells and is not present in normal somatic tissues.

Thus induction of telomerase is postulated to be a key component in the progression of a premalignant condition to malignancy. Without wishing to be bound by any theory it is postulated that inhibition of telomerase in an immortalized cell line or in the malignant condition would cause senescence or cell death if the cell depended on telomerase to compensate for loss of telomeric DNA through cell division.

The RNA moiety of human telomerase contains the 5'-CCCTAA-3' SEQ ID NO: 5 sequence that may act as the template for denovo synthesis. The enzyme also contains a region that recognizes the guanine rich single strands of DNA substrate.

Applicants have discovered a synthetic oligonucleotide which inhibits telomerase and leads to cell death in neoplastic cells. In one aspect the invention contemplates a method for treating conditions or diseases in vitro or in vivo which are related to the ability of a cell to remain immortal. Examples of such cells include cancerous cells which are somatic cells which have regained the ability to express telomerase, primarily associated with treatment of cancers of any type including solid tumors and leukemias including those in which cells are immortalized such as apudoma, choristoma, branchioma, malignant carcinoid syndrome, carcinoid heart disease, carcinoma (e.g., Walker, basal cell, basosquamous, Brown-Pearce, ductal, Ehrlich tumor, in situ, Krebs 2, merkel cell, mucinous, non-small cell lung, oat cell, papillary, scirrhous, bronchiolar, bronchogenic, squamous cell, and transitional cell), histiocytic disorders, leukemia (e.g., b-cell, mixed-cell, null-cell, T-cell, T-cell chronic, HTLV-II-associated, lyphocytic acute, lymphocytic chronic, mast-cell, and myeloid), histiocytosis malignant, Hodgkin's disease, immunoproliferative small, non-Hodgkin's lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing's sarcoma, synovioma, adenofibroma, adenolymphoma, carcinosarcoma, chordoma, mesenchymoma, mesonephroma, myosarcoma, ameloblastoma, cementoma, odontoma, teratoma, thymoma, throphoblastic tumor, adenocarcinoma, adenoma, cholangioma, cholesteatoma, cylindroma, cystadenocarcinoma, cystadenoma, granulosa cell tumor, gynandroblastoma, hepatoma, hidradenoma, islet cell tumor, leydig cell tumor, papilloma, sertoli cell tumor, theca cell tumor, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, antiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyllodes, fibrosarcoma, hemangiosarcoma, leiomyosarcoma, leukosarcoma, liposarcoma, lymphangiosarcoma, myosarcoma, myxosarcoma, ovarian carcinoma, rhabdomyosarcoma, sarcoma (e.g., Ewing's experimental, Kaposi's, and mast-cell), neoplasms (e.g., bone, breast, digestive system, colorectal, liver, pancreatic, pituitary, testicular, orbital, head and neck, central nervous system, acoustic, pelvic, respiratory tract, and urogenital), neurofibromatosis, and cervical dysplasia), and for treatment of other conditions in which cells have increased proliferation. For example, HIV infected animals exhibit exhibit increased proliferation of CD4+ cells. The invention could thus be used to quell this increased proliferation. Those of skill in the art will readily appreciate that other diseases so characterized can be treated by the method of the invention.

Oligonucleotides can be designed either to bind to a telomere (to block the ability of telomerase to bind to that telomere and thereby extend that telomere), or to bind to the resident oligonucleotide (RNA) present in telomerase and to thereby block telomerase activity on any nucleic acid (telomere).

Cells or disease states more specifically treatable by the method of the invention can be identified by an in vitro assay of the cells for telomerase activity. There are numerous assays available in the art to determine the presence of telomerase in a particular cell line or tumor. Tumor cells in vivo may be simply removed and tested for presence of telomerase or the in vitro cell line may be used. One such assay is listed in Science, Vol. 266, Dec. 23, 1994, Nam W. Kim, et al., "Specific Association of Human Telomerase Activity With Immortal Cells and Cancer", pp. 2011–2014. See also Prowse, Karen R. et al., "Identification of a nonprocessive telomerase activity from mouse cells" P.N.A.S. Vol 90 Pp. 1493–1497, February 1993. Generally, assay methods include hypotonic swelling and physical disruption of cells requiring $10^7$ to $10^8$ cells and extraction by detergent lysis. A more sensitive recently developed assay includes PCR based assay wherein telomerase synthesized extension products serve as templates for PCR amplification which can be performed in a single reaction.

Quite unexpectedly applicants have discovered that an oligonucleotide of only 6 bases (one telomere repeat motif) (5'-d(TTAGGG)-3') SEQ ID NO: 3 exhibits marked decrease in tumor cell proliferation. This is an unexpected result as traditional oligonucleotide therapy postulates stable hybridization of the oligonucleotide to endogenous target sequences. It is generally thought that at least at physiological salt and at 37° C. oligonucleotides of less than 12 bases will not form stable hybrid duplexes. Oligonucleotides of this short length will not form stable hybrid duplexes at 37° C. possibly indicating a non-antisense type mechanism contributes to telomerase inhibition.

For example, PCT application international publication No. WO 93/23572 discusses cellular senescence and immortalization via the activity of telomeres and telomerase. While the invention is primarily drawn to diagnostic methods of measuring telomere length in characterizing neoplastic cells, it discusses the concept of hybridization of oligonucleotides to telomere or telomerase. The application specifically limits such oligos to at least two or more and not more than 50 telomere motif repeats (between 12 and 300 bases). Further when a cell line was treated with an oligonucleotide, 5'-d(TTAGGG)$_2$-3' SEQ ID NO: 6 it required as many as 6 days in culture before any observable response was obtained. The application concludes that an oligonucleotide must be chosen which binds to telomerase at a different site than that bound by the (5'-d(TTAGGG)$_2$-3') SEQ ID NO: 6 oligo for any desirable inhibition of replicative capacity.

Applicants have discovered quite unexpectedly that an extremely short oligonucleotide 5'-d(TTAGGG)-3' will inhibit telomerase with observable S-phase delay in the cell cycle and a dramatic increase in apoptotic cell death.

Applicants have found that the telomere sequence phosphorothioate-modified single repeat 6-mer 5'-d(TTAGGG)-3' in fact, can work better than longer oligos with more repeats. While not wishing to be bound by any theory it is postulated that efficacy of oligonucleotide inhibition is length-dependent with regard to uptake and ultimately elimination of immortal phenotype. Such shorter oligonucleotides are less expensive, easier to synthesize, and less likely to cause toxicity. The following examples are for illustrative purposes only and in no way are intended to limit the invention.

Applicants have discovered that the oligonucleotides of the invention lead to a substantial S-phase delay in the cell cycle which can lead to apoptosis. As such, concomitant use of other therapeutic agents such as antimetabolites (5-fluorouridine, 6-thioguanine or methotrexate) which also cause an S-phase delay but by independent mechanisms would show additive (possibly synergistic) therapeutic utility with the TELIGO. Thereby increasing efficacy while reducing the dose required to produce a therapeutic response and also reducing toxicity through a smaller body burden of the therapeutic agents.

As used herein the terms TELIGO means the 6-mer oligonucleotide which mimics the telomere motif (5'-d(TTAGGG)-3') SEQ ID NO: 3.

The oligonucleotide of the invention can be any of 6 sequential bases making up the telomere repeats. For example the following oligos would be expected to have the same effects as 5'-d(TTAGGG)-3' SEQ ID NO: 3: (TAGGGT) SEQ ID NO: 7; (AGGGTT) SEQ ID NO: 8; (GGGTTA) SEQ ID NO: 9; (GGTTAG) SEQ ID NO: 10; (GTTAGG) SEQ ID NO: 11 and their complements.

EXAMPLE 1

In Vitro Data

A cell line, OMA-BL1, of cells derived from an American Burkitt's lymphoma patient, which had the typical 8:14 chromosome translocation characteristic of Burkitt's lymphoma was tested according to the method of the invention. The OMA-BL1 cells have a homologous staining region along chromosome 18 (18 HSR). The cell line was grown in vitro consisting of RPMI 1640 medium supplemented with 20% fetal calf serum (RF20). 2 mM L-glutamine and antibiotics (streptomycin 100 µ/ml and penicillin) 2× week.

Phosphorothioate oligonucleotides corresponding to the recognition sequence for telomerase enzyme were synthesized. The sequence of oligonucleotides tested was 5'-(TTAGGG)-3' SEQ ID NO: 3. They were dissolved in RPMI1640 medium before using.

The cell lines were grown under concentration of $5 \times 10^5$ cells/ml and RPMI1640 with and without different concentrations of oligo. Concentrations of oligo used in the study were 1.25 µM and 2.5 µM. The growth rate of the cells was measured by counting the cells with a light microscope and Neuber cell counter on days 1, 3, and 5 after initiation of the culture.

Figure 2:
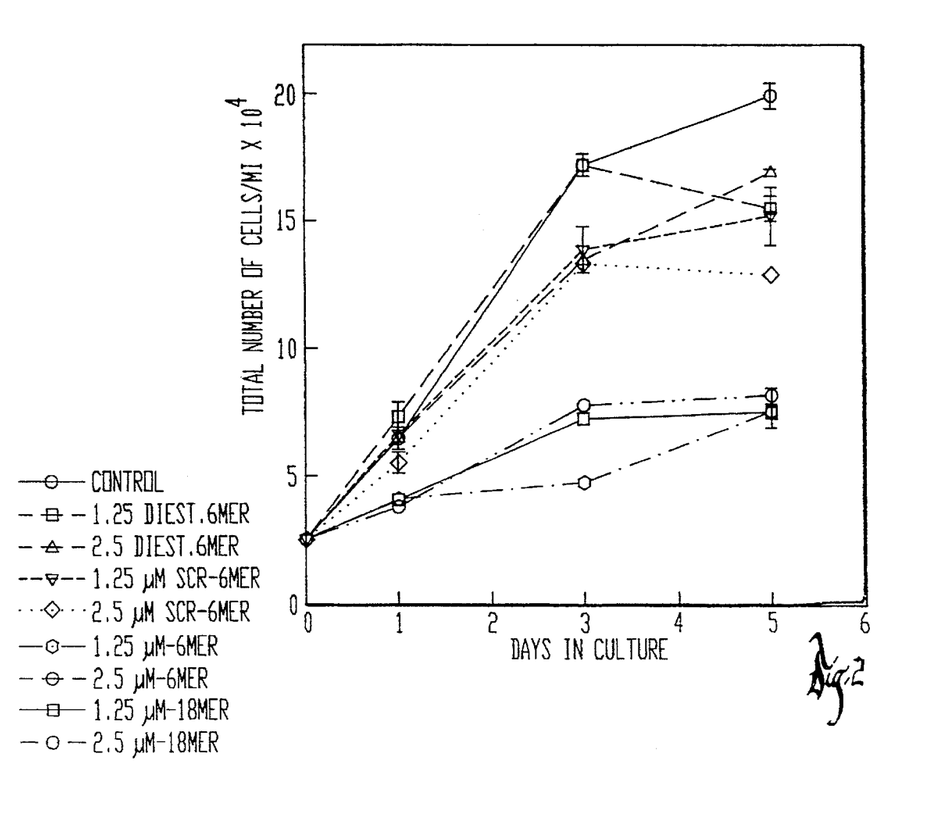
FIG. 2 is a graph depicting the in vitro results of Burkitt's lymphoma cells treated with a diester oligo, a scrambled 6-mer, and an 18-mer at concentrations of 1.25 and 2.5 μM.

Results are shown in the FIG. 2. As can be seen in FIG. 2, incubation of the oligos with the OMA-BL1 cells was tested using a control (no oligo) a phosphorothioate and a diester 6-mer 5'-d(TTAGGG)-3' SEQ ID NO: 3 at two different concentrations 1.25 µM and 2.5 µM, a scrambled 6-mer (TGTGAG) SEQ ID NO: 12 and an 18-mer 5'-d(TTAGGG)$_3$-3'SEQ ID NO: 4 phosphorothioate oligonucleotide. As can be seen in Table 1, the phosphorothioate 6-mer exhibited significant decrease in cell proliferation.

TABLE 1

| | Doubling Time (Hours of Doubling) | |
|---|---|---|
| Oligonucleotide Sequence | 1.25 µM | 2.5 µM |
| Media Control (no oligonucleotide) | 45.9 ± (9) | |
| 5'-d(TTAGGG)-3'SEQ ID NO:3 | 59.4 ± 7.5(6)* | >100(6)*# |
| 5'-d(TGTGAG)-3'SEQ ID NO:12 | 42.4 ± 1.8(3) | 40.9 ± 2.3(3) |
| 5'-d(GTTGAGGGG)-3'SEQ ID NO:13 | 49.4 ± 4.02(3 | 60.71 ± 4.25(3) |
| 5'-d(TGAGG)-3'SEQ ID NO:14 | 30.3 ± 39 (3) | 42.0 ± 6.8(3) |
| 5'-d(TAGGG)-3'SEQ ID NO:15 | 48.5 ± 3.0(3) | 41.6 ± 2.0(3) |
| 5'-d(TTAGG)-3'SEQ ID NO:16 | 31.2 ± 8.5(3) | 36.7 ± 3.1(3) |
| 5'-d(TCCTAGGTCCATGTCGTACGC)-3'SEQ ID NO:17 | nd | 38(3) |
| 5'-d(TTAGGGTTAGGG):'SEQ ID NO:16 | >100(3)* | >100(3)* |

TABLE 1-continued

| Oligonucleotide Sequence | Doubling Time (Hours of Doubling) | |
| --- | --- | --- |
| | 1.25 µM | 2.5 µM |
| 5'-d(TTAGGGTTAGGGTTAGGG)-3'SEQ ID NO:4 | >100(3)* | >100(3)* |
| 5'-d(TTAGGGTTAGGGTTAGGGTTAGGG)-3'SEQ ID NO:18 | >100(3)* | >100(3)* |

*significantly different from control
Numbers in parenthesis are the number of times the experiment was repeated
Numbers >100 indicate S-phase substantially > than 100 hours. Cells were observed for 5 days.
As can be seen from table, the TTAGGG TELIGO shows significantly increased doubling time compared to media control, oligo control and 5-mers.

An observable difference in treated and non treated cells was observed in as little as one day. Finally, two 5-mer oligos TTAGG and TAGGG were tested and there was no inhibitory effect.

Cytomorphological Analysis

Cytocentrifuge preparation of the control on telo-ODN treated cells were made and stained with Wright/Giemsa stain. The cells were examined for their cytomorphology using a light microscope.

EXAMPLE 2

Figure 3:
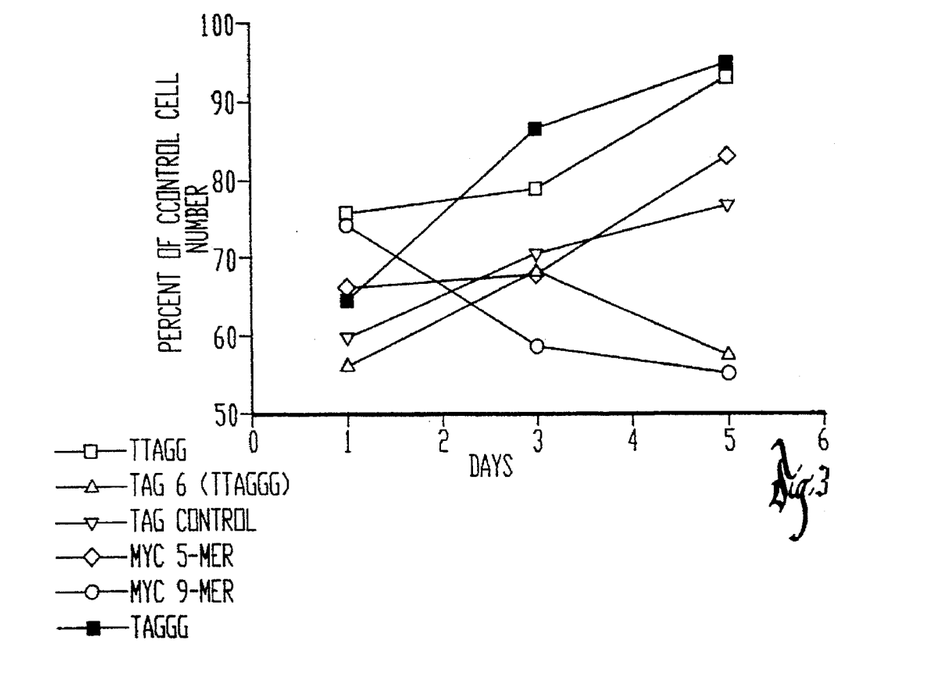
FIG. 3 is a graph of Burkitt's lymphoma cells treated with the 6-mer, a control with no oligo, a scrambled 6-mer control and portions from a myc antisense oligo containing a telomere motif.

FIG. 3 depicts a similar test run on OMA BL-1 cells with the 6-mer, a control (no oligo) the scrambled 6-mer and an antisense oligo to the c-myc gene, previously known to have significant efficacy in reduction of proliferation. The oligo had within it a sequence substantially analogous to the telomere motif shown in bold, and the portion surrounding the analogous region was tested. This included the myc 5-mer (TGAGG) SEQ ID NO: 14 and 9-mer TGTGAGGGG SEQ ID NO: 19 derived from the antisense oligo c-myc 5'AACGGTGAGGGGCAT-3'SEQ ID NO: 20. FIG. 3 is a graph depicting results on cell proliferation after several days, as the percent of control cell number. As can be seen, the 6-mer 5'-d(TTAGGG)-3' SEQ ID NO: 3 has significant effects drastically decreasing cell proliferation from that compared to the other oligos. Interestingly the myc 9-mer had effects similar to the 6-met, suggesting that a telomere motif or even a substantially analogous motif embedded in a traditional oligonucleotide targeting a different genetic region can have potent affects. Thus an embedded telomere sequence in an antisense oligonucleotide could result in therapeutic agent with multiple favorable mechanisms of action.

In another experiment the c-myc (discussed earlier) and a c-myb antisense oligonucleotide (5'TATGCTGTGCCGGGG<u>TCTTCGGGC</u>-3' SEQ ID NO: 21 also observed to contain a telomere motif were tested. A 9-mer containing the motif was tested (underlined above). Both showed significantly decreased cellular proliferation. Also surprisingly telomerase activity was inhibited with the 9-mer from the antisense c-myc sequence.

EXAMPLE 3

Chang cells (human liver carcinoma) were grown in three T150 flasks until they reached confluency. 5'-d(TTAGGG)-3' SEQ ID NO: 3 phosphorothioate oligonucleotide was added at 3 µM concentration to each of the flasks and was allowed to incubate for three hours. Cells were harvested by scraping with a rubber policeman. Telomerase enzyme was prepared according to the method of Dignam, J. D.; Lebovitz, R. M.; and Raeder, R. G. (1983). Accurate transcription initiation by RNA Polymerase II in a Soluble Extract From Isolated Mammalian Nuclei. Nucl. Acids Res. 11, 1475–1489. 20 µL samples were taken from –80° C. and 20 µL of a reaction mixture containing 4.0mM dATP, 4.0mM dTTP, 4.0 mM dGTP, 2.0 µM (5'-d(TTAGGG)$_3$ -3') SEQ ID NO: 4 primer, 10 mM β-mercaptanol, 100 mM TRIS-acetate pH 8.5, 2.0 mM MgCl$_2$, 1 mM spermidine, and 2 µL of 3000 Ci/mmol P$^{32}$ labeled dGTP.

Samples were incubated for 30 minutes at 30° C. and stopped by the addition 10 µL 5.0M EDTA pH 8.0 and 2.0 µL of tracking dye. Samples were loaded onto a 12.5 percent acrylamide gel and run at 25 mA constant power for 4–5 hours until the tracking dye had run off the gel. The gel was then soaked in 10 percent glycerol and water and dried overnight between two sheets of cellophane. An autoradiograph was of the dried gel showed elongation by telomerase in the control lane. The telomerase activity was inhibited for the 6-mer oligo.

EXAMPLE 4

Cellular Uptake Comparison of
5'-d(TTAGGG)n -3'SEQ ID NO: 3

Figure 4A:
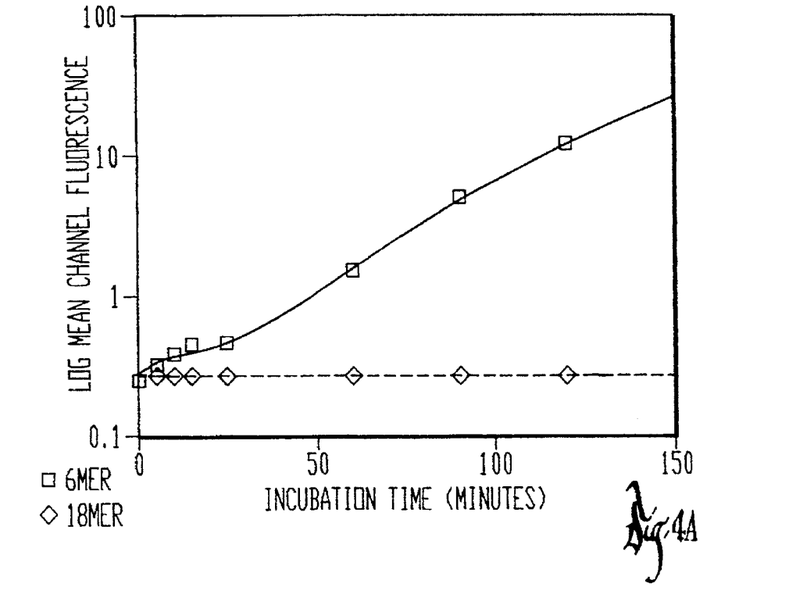
FIG. 4A, B, and C is a graph measuring oligo uptake of FITC-labeled cells in Burkitt's lymphoma cells of the 6-mer (5'-d(TTAGGG)-3') and 18-mer (5'-d(TTAGGG)-3')$_3$ SEQ ID NO: 4
Figure 4B:
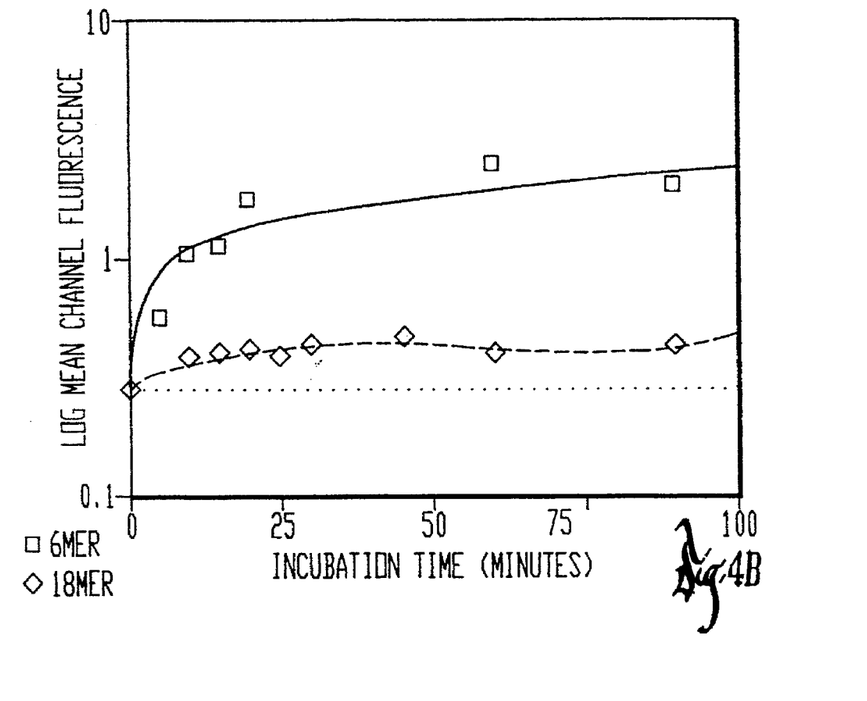
Figure 4C:
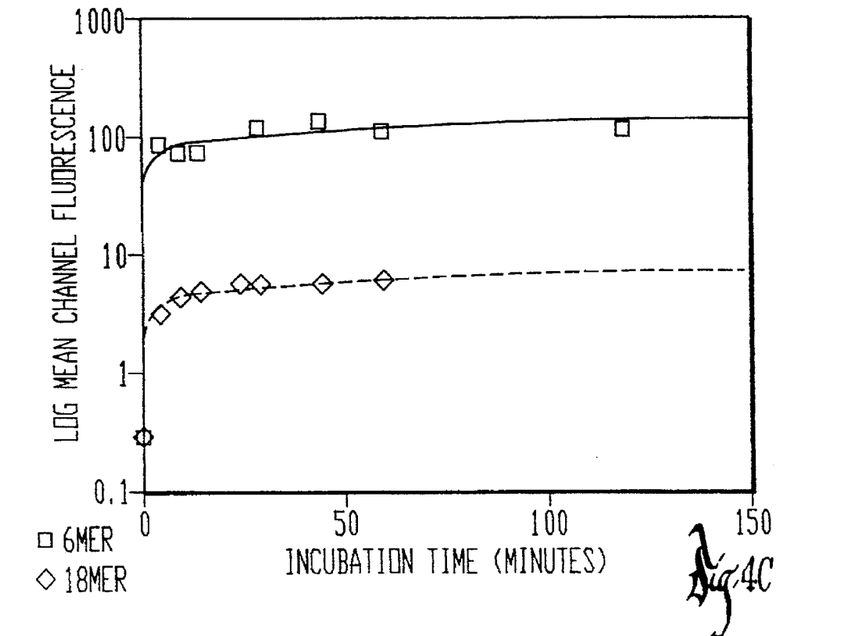
Figure 5:
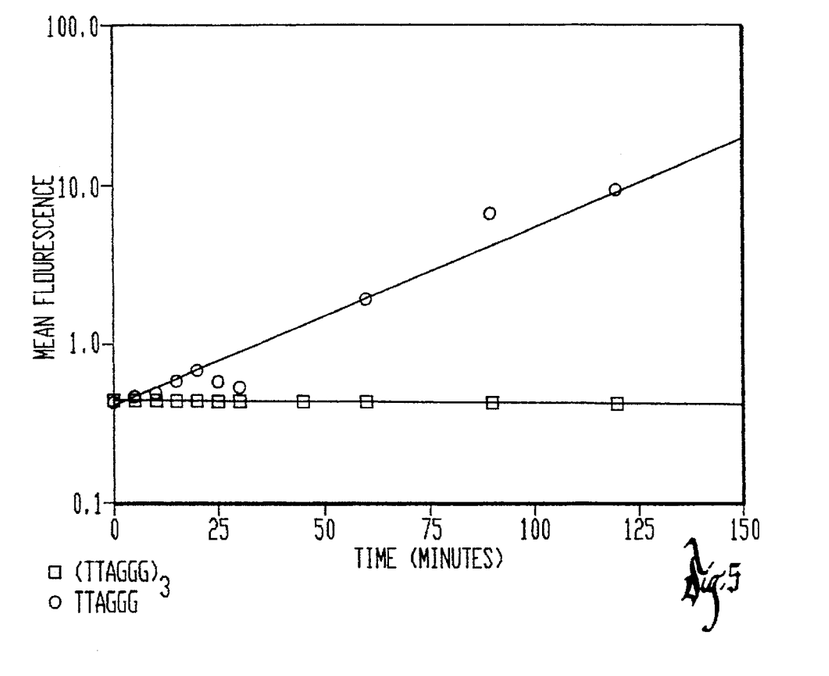
FIG. 5 is a graph measuring oligo uptake of FITC-labeled cells for the 6-mer and 18-mer.
Figure 6:
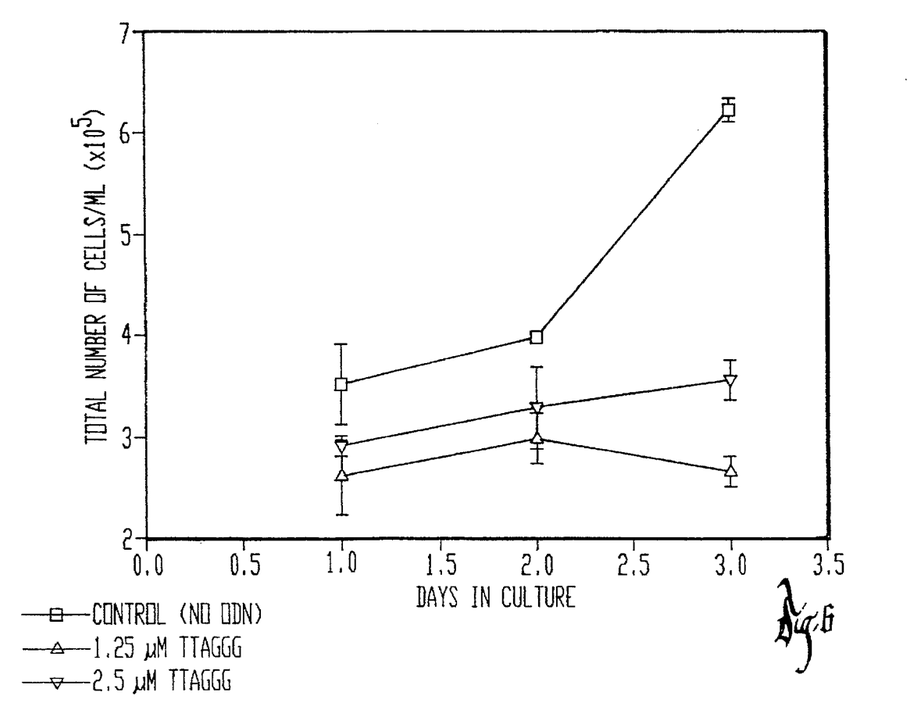
FIG. 6 is a graph depicting Burkitt's lymphoma cells treated with the 6-mer(5'-d(TTAGGG)-3') SEQ ID NO: 3 at 1.25 μM and at 2.5 μM

Several studies were done on cellular uptake and thus efficiency of oligonucleotide sequences mimicking the telomere motif. FIGS. 4 and 5 depict the comparison of the 18-mer 5'-d(TTAGGG)$_3$ -3' SEQ ID NO: 4 with the 6-mer TELIGO 5'-d(TTAGGG)-3' SEQ ID NO: 3 for cellular uptake of FITC-labeled oligo in OMA-BL1 cells (FIGS. 5 and 4(a)), PBE1 cells FIG. 4(b) and in the nondifferentiated HPB-null cell line FIG. 4(c). As can be seen, the 6-mer has considerably higher cellular uptake in cell lines which have differentiated. FIG. 6 depicts the effects of 5'-d(TTAGGG) -3' SEQ ID NO: 3 on growth of OMA-BL1 cells in vitro at 1.25 µM and 2.5 µM.

Finally, Table 1 depicts various oligonucleotide phosphorothioate modified oligonucleotides and their effect on doubling time of OMA-BL1 cells.

EXAMPLE 5

Reduction in Metastasis

An experiment was run on two highly metastatic breast cancer cell lines, one human the other mouse, and demonstrated not only inhibition of proliferation but also decrease in invasion for the 5'-d(TTAGGG)-3' SEQ ID NO: 3 and the 5'-d(TTAGGG)$_3$ -3' SEQ ID NO: 4 phosphorothioate oligos.

It has been repeatedly demonstrated that there is a good correlation between tumor invasion and metastasis. Yagel, S., Khokha, R., Denhardt, D. T., Kerbel, R. S., Parhar, R. S. and Lala, P. K. Mechanism of Cellular Invasiveness: A Comparison of Amnion Invasion In Vitro and Metastatic Behavior In Vivo. J. Natl. Cancer. Inst., 81:768–775, 1989.

Tumor Invasion Assay

Migration of 410.4 cells through matrigel coated Nucleopore filters was measured using Matrigel invasion chambers (Collaborative Biomedical Products). These chambers contained inserts with 8 µM pore size and were coated with a uniform film of matrigel. $4 \times 10^4$ 410.4 cells in Weymouths Medium plus 0.1% bovine serum albumin were added to the invasion chambers. The wells below the invasion chambers contained 0.5 ml of Weymouths plus 10% fetal calf serum as a chemoattractant. The chambers were incubated for 48 hours at 37° to allow the cells to invade through the matrigel into the lower wells. The noninvasive cells were then removed from the upper surface of the membrane with a cotton swab and the cells on the lower surface were stained using a Leucostat staining kit. The membranes then were removed from the chamber using a scalpel and the cells were counted under high power (450×) in 5 random fields.

Results are shown in Table 2 below:

TABLE 2

| Cell line | Oligo | % control invasion | % inhibition |
| --- | --- | --- | --- |
| Human | 6-mer | 30 | 70 |
| Human | 18-mer | 8 | 92 |
| Mouse | 6-mer | 15 | 75 |
| Mouse | 18-mer | 21 | 79 |

EXAMPLE 6

In Vivo Data

Figure 7:
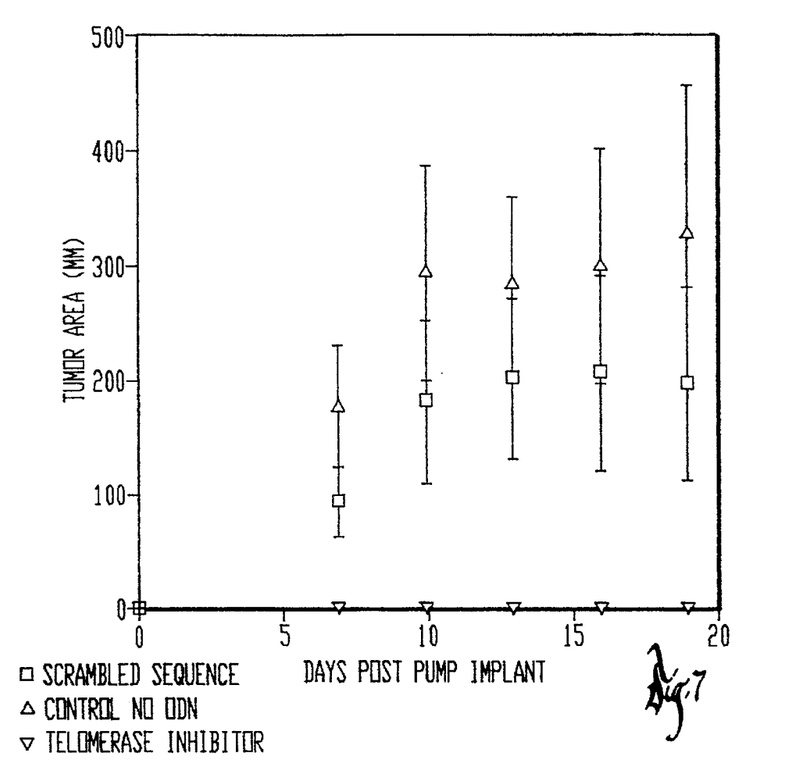
FIG. 7 is a graph depicting in vivo results of a mouse treated with the 6-mer (5'-d(TTAGGG)-3')SEQ ID NO: 3, a control (no oligo) and a scrambled 6-mer.

FIG. 7 is a depiction of the TELIGO 5'-d(TTAGGG)-3' SEQ ID NO: 3 in mice with OMA-BL1 cells. The experiment was designed to evaluate the acute toxicity and pharmacokinetics of antisense phosphorothioate oligonucleotides shown to have telomerase-inhibiting in vitro effects mimicking the telomere.

A. In vivo Efficacy in mouse tumor models

1. OMA-BL1, Burkitt's Lymphoma in Nude Mice

Nude mice were injected with $5 \times 10^6$ OMA-BL1 cells subcutaneously in the leg flank. The mice were observed daily for the appearance of tumors and general well-being. Once the tumors were of sufficient size (approximately 3 weeks), Alzet mini pumps (Model 2002, 0.5 µl/hour for 14 days) were implanted. The mean fill volume of these pumps is 0.226 ml. A solution of 4 mg/ml of 6-mers and 20 µl of FITC-TAG-6 was prepared then sterile filtered through a 0.22 µm in line filter (Millipore). The filtrate was passed directly into the Alzet pump to provide a delivery of 2 µg/hour for each 24 hours for a total of 48 µg/mouse/day and 672 µ/mouse total. The following matrix was evaluated:

| Group | Number per group | Dose/ Duration |
| --- | --- | --- |
| Control | 5 | None |
| 5'-d(TTAGGG)-3'SEQ ID NO:3; TAG-6 | 4 | 48 µg/day/ 14 Days |
| 5'-d(TGTGAG)-3'SEQ ID NO:12 SCR-6 | 4 | 48 µa/day/ 14 Days |

From the results shown in FIG. 7, continuous subcutaneous infusion of a telomere motif (5'-d(TTAGGG)-3' SEQ ID NO: 3) oligonucleotide in tumor bearing (Burkitt's lymphoma) nude mice resulted in localization of the oligonucleotide in tumors. No toxicity was observed during the treatment and as shown in FIG. 7 regression of tumors in TELIGO treated mice was seen, with no such action was observed for the scrambled oligo indicated a sequence specific interaction. It is postulated that similar results would be seen in vivo as well as with other telomere motifs having repeats up to any length that would still be taken up by cells (i.e. up to about 15 repeats).

EXAMPLE 7

An FAM labeled 6-mer 5'-d(TTAGGG)-3' SEQ ID NO: 3 was injected into nude mice with Burkitt's lymphoma (OMA-BL1) cells growing in them. The FAM labeled TELIGO was recovered from the urine of a nude mouse bearing a tumor composed of OMA-BL1 cells. The urine was evaluated on an Applied Biosystem, Inc. Gene Scanner which can separate the products of the telomerase enzyme by size along the abscissa and reports the quantity of products by the fluorescence intensity along the ordinate in arbitrary units. An internal standard of rhodamine labeled nucleic acids is run in the same gel in order to establish the measurement of size of the telomerase enzyme products of the TELIGO. The FAM label verifies that the DNA is from the injected TELIGO 6-mer and the size additions of intervals of 6-base lengths is evidence of the telomerase enzyme activity which adds 6 bases per catalytic cycle.

Figure 8:
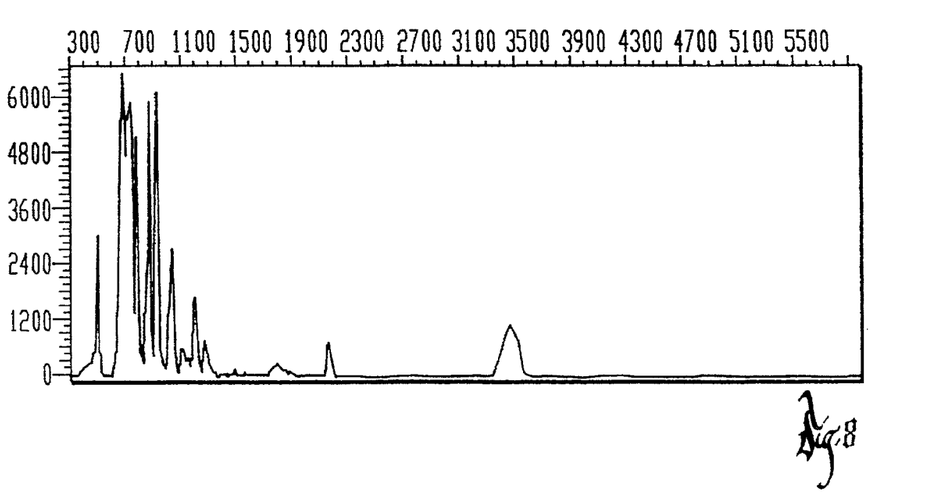
FIG. 8 is a graph of the relative sizes of FAM labeled TELIGO 6-mer recovered from the urine of a nude mouse bearing a tumor composed of OMA-BL-1 cells.

Analysis of the tissue, blood and urine revealed a shift in molecular size of the 6-mer. Analysis of products from the urine showed that a higher molecular weight of FAM-labeled product were present including products with an apparent size of a 12-mer (one addition), 19-mer (two additions), 24-mer (three additions), 36-mer (five additions), 54-mer (eight additions), 61-mer (nine additions), 148-mer (twenty-four additions), 257-mer (forty-two additions), and 322-mer (fifty-three additions). All products were multiples of six which is significant because in that telomerase adds bases to telomeres in multiples of six. Thus it would seem the 6-mer interacts with telomerase to form unique products verifying interaction in vivo. Results are shown in FIG. 8. These data are evidence that the TELIGO 6-mer is a substrate for telomerase in vivo.

EXAMPLE 8

Figure 9:
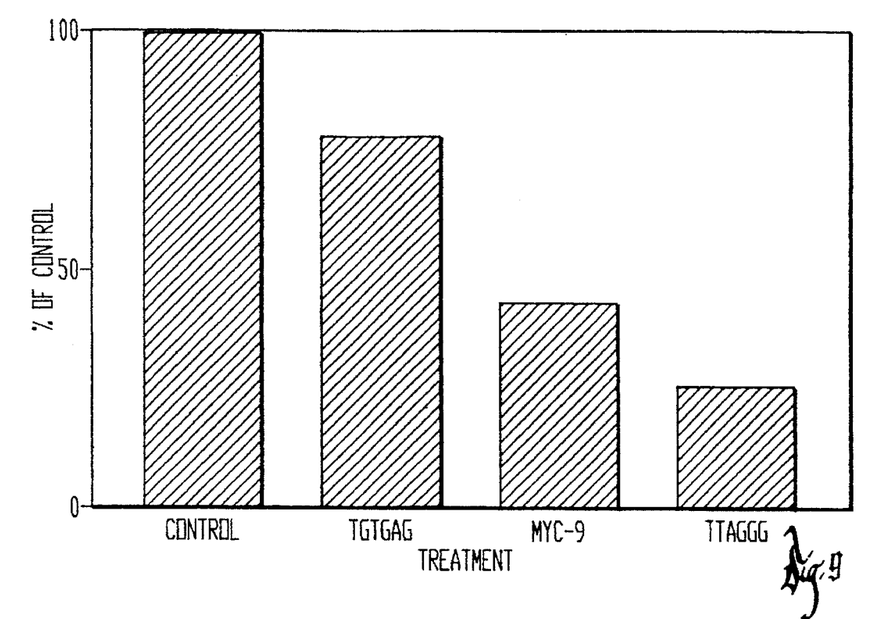
FIG. 9 is a graph showing the telomerase activity in vitro.

An OMA-BL1 cell lysate was prepared to retain telomerase activity. The telomerase enzyme adds radioactive nucleic acids to the substrate which are separated on a polyacrylamide gel. The relative radioactivity in the gel was measured by densitomitry of the autoradiograph. The results are shown in FIG. 9. The 6-mer inhibits the activity to approximately 25% of control value, the myc 9-mer which contains the TELIGO sequence inhibits the activity to approximately 45% of control and a scrambled phosphorotioate with the same composition of bases shows a modest inhibition to approximately 80% of control.

EXAMPLE 9

Figure 10:
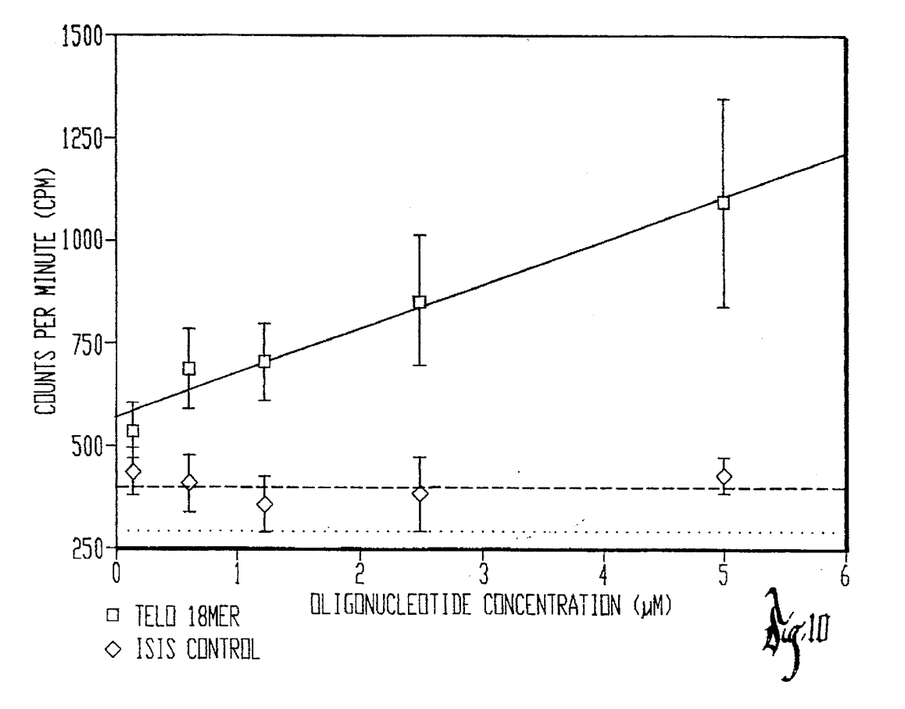
FIG. 10 is a graph depicting the relative radioactivity retained in a cell lysate following incubation of the cells with the 18-mer 5'-d(TTAGGG)$_3$-3'SEQ ID NO: 4.

In a final experiment, a HPB-null cell lysate is incubated with the TELIGO 18-mer (5'-d(TTAGGG)$_3$-3' SEQ ID NO: 4 (FIG. 10). The rate of cellular incorporation of labeled nucleic acids is demonstrated in the ISIS 1082 control which does not contain the TELIGO sequence. The extension on the TELIGO 18-mer are dependent upon the dose of TELIGO in which the living cells are incubated. FIG. 10 demonstrates both the sequence specificity and dosedependence of the TELIGO for telomerase recognition and telomere sequence additions.

The results of FIGS. 8, 9 and 10 show that the TELIGO 6 and 18-mer possess very similar properties in the inhibition of telomerase enzyme activity. FIG. 8 measures the inhibition of the telomerase activity directly while FIG. 9 shows the dose relationship between the 18-mer and telomerase recognition of the TELIGO as a substrate. This would define the TELIGOs as competative inhibitors of telomerase. FIG. 10 extends the property of telomerase inhibition to the 6-mer in vivo in which like FIG. 9 the 6-mer is measured as the apparent product of telomerase activity and would be a competiive inhibitor in vivo.

What is claimed is:

1. A method of inhibiting proliferation of and/or killing cells characterized by uncontrolled proliferation comprising:
   contacting said cells with an oligonucleotide, said oligonucleotide having a nucleotide sequence consisting of a single human telomeric repeat motif.

2. The method of claim 1 wherein said cell is characterized by telomerase activity.

3. The method of claim 1 wherein said oligonucleotide is modified to resist enzyme degradation.

4. The method of claim 1 wherein said oligonucleotide has a phosphorothioate backbone modification.

5. The method of claim 1 wherein said cells are Burkitt's lymphoma or Chang cells.

6. The method of claim 1 wherein said oligonucleotide is a deoxyribonucleotide.

7. The method of claim 1 wherein said repeat is TTAGGG.

8. A method of inhibiting proliferation of and/or killing cells characterized by telomerase expression comprising:
   contacting said cells with an oligonucleotide that inhibits expression of a sequence other than a telomere motif, said oligonucleotide comprising a sequence substantially analogous to a human telomere motif, wherein said oligonucleotide targets the C-myb gene.

9. The method of claim 8 wherein said telomere motif is selected from the group consisting of TGAGGG and TTCGGG.

10. The method of claim 8 wherein said oligonucleotide is a phosphorothioate oligonucleotide.

11. A method of inhibiting proliferation of cells which express telomerase comprising:
   contacting said cells with an oligonucleotide which mimics a telomere motif, said oligonucleotide having a sequence selected from the group consisting of TTAGGG (SEQ ID NO: 3), TAGGGT (SEQ ID NO: 7), AGGGTT (SEQ ID NO: 8), GGGTTA (SEQ ID NO: 9), GGTTAG (SEQ ID NO: 10), and GTTAGG (SEQ ID NO: 11).

12. The method of claim 11 wherein said oligonucleotide is modified to resist enzyme degradation.

13. The method of claim 11 wherein said oligonucleotide has a phosphorothioate backbone modification.

14. The method of claim 11 wherein said cells are Burkitt's lymphoma or Chang cells.

15. The method of claim 11 wherein said oligonucleotide is a deoxyribonucleotide.

16. The method of claim 11 wherein said repeat is TTAGGG.

17. The method of claim 11 wherein said oligonucleotide is a phosphorothioate oligonucleotide.

18. A pharmaceutical composition for inhibiting diseases characterized by uncontrolled proliferation of cells comprising:
   a pharmaceutically effective amount of an oligonucleotide, said oligonucleotide having a sequence consisting of a single human telomere motif said motif selected from the group consisting of SEQ ID NOS: 3, 7, 8, 9, 10 and 11, and
   a pharmaceutical carrier.

19. A method of inhibiting proliferation of and/or killing cells characterized by telomerase activity comprising:
   contacting said cells with an oligonucleotide, said oligonucleotide having no more than one consecutive repeat sequence which mimics a human telomeric repeat motif.

20. The method of claim 19 wherein said oligonucleotide is modified to resist enzyme degradation.

21. The method of claim 19 wherein said oligonucleotide has a phosphorothioate backbone modification.

22. The method of claim 20 wherein said cells are Burkitt's lymphoma or Chang cells.

23. The method of claim 20 wherein said oligonucleotide is a deoxyribonucleotide.

24. The method of claim 20 wherein said repeat is TTAGGG.

25. A method of inhibiting proliferation of and/or killing cells characterized by telomerase expression comprising:
   contacting said cells with an oligonucleotide that inhibits expression of a sequence other than a telomere motif, said oligonucleotide comprising a sequence substantially analagous to a human telomere motif, said sequence selected from the group consisting of TGAGGG and TTCGGG.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:1:

TTGGGG        6

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:2:

CCCCAA        6

( 2 ) INFORMATION FOR SEQ ID NO:3:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:3:

TTAGGG        6

( 2 ) INFORMATION FOR SEQ ID NO:4:

( i ) SEQUENCE CHARACTERISTICS:
        ( A ) LENGTH: 18 base pairs
        ( B ) TYPE: nucleic acid ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:4:

TTAGGGTTAG GGTTAGGG                                                                                             18

( 2 ) INFORMATION FOR SEQ ID NO:5:

( i ) SEQUENCE CHARACTERISTICS:
                ( A ) LENGTH: 6 base pairs
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:5:

CCCTAA                                                                                                          6

( 2 ) INFORMATION FOR SEQ ID NO:6:

( i ) SEQUENCE CHARACTERISTICS:
                ( A ) LENGTH: 12 base pairs
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:6:

TTAGGGTTAG GG                                                                                                   12

( 2 ) INFORMATION FOR SEQ ID NO:7:

( i ) SEQUENCE CHARACTERISTICS:
                ( A ) LENGTH: 6 base pairs
                ( B ) TYPE: nucleic acid
                ( C ) STRANDEDNESS: single
                ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:7:

TAGGGT                                                                                                          6

( 2 ) INFORMATION FOR SEQ ID NO:8:

( i ) SEQUENCE CHARACTERISTICS:
                ( A ) LENGTH: 6 base pairs
                ( B ) TYPE: nucleic acid
                ( C ) STRANDEDNESS: single
                ( D ) TOPOLOGY: linear ( i i ) MOLECULE TYPE: other nucleic acid (i i i) HYPOTHETICAL: NO (i v) ANTI-SENSE: NO (x i) SEQUENCE DESCRIPTION: SEQ ID NO:8:

AGGGTT                                                                                                                                6

(2) INFORMATION FOR SEQ ID NO:9:

(i) SEQUENCE CHARACTERISTICS:
        (A) LENGTH: 6 base pairs
        (B) TYPE: nucleic acid
        (C) STRANDEDNESS: single
        (D) TOPOLOGY: linear     (i i) MOLECULE TYPE: other nucleic acid     (i i i) HYPOTHETICAL: NO     (i v) ANTI-SENSE: NO     (x i) SEQUENCE DESCRIPTION: SEQ ID NO:9:

GGGTTA                                                                                                                                6

(2) INFORMATION FOR SEQ ID NO:10:

(i) SEQUENCE CHARACTERISTICS:
        (A) LENGTH: 6 base pairs
        (B) TYPE: nucleic acid
        (C) STRANDEDNESS: single
        (D) TOPOLOGY: linear     (i i) MOLECULE TYPE: other nucleic acid     (i i i) HYPOTHETICAL: NO     (i v) ANTI-SENSE: NO     (x i) SEQUENCE DESCRIPTION: SEQ ID NO:10:

GGTTAG                                                                                                                                6

(2) INFORMATION FOR SEQ ID NO:11:

(i) SEQUENCE CHARACTERISTICS:
        (A) LENGTH: 6 base pairs
        (B) TYPE: nucleic acid
        (C) STRANDEDNESS: single
        (D) TOPOLOGY: linear     (i i) MOLECULE TYPE: other nucleic acid     (i i i) HYPOTHETICAL: NO     (i v) ANTI-SENSE: NO     (x i) SEQUENCE DESCRIPTION: SEQ ID NO:11:

GTTAGG                                                                                                                                6

(2) INFORMATION FOR SEQ ID NO:12:

(i) SEQUENCE CHARACTERISTICS:
        (A) LENGTH: 6 base pairs
        (B) TYPE: nucleic acid
        (C) STRANDEDNESS: single
        (D) TOPOLOGY: linear     (i i) MOLECULE TYPE: other nucleic acid     (i i i) HYPOTHETICAL: NO     (i v) ANTI-SENSE: NO ( x i ) SEQUENCE DESCRIPTION: SEQ ID NO:12:

TGTGAG                                                                                                        6

( 2 ) INFORMATION FOR SEQ ID NO:13:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:13:

GTTGAGGGG                                                                                                     9

( 2 ) INFORMATION FOR SEQ ID NO:14:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:14:

TGAGG                                                                                                         5

( 2 ) INFORMATION FOR SEQ ID NO:15:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:15:

TAGGG                                                                                                         5

( 2 ) INFORMATION FOR SEQ ID NO:16:

( i ) SEQUENCE CHARACTERISTICS:
        ( A ) LENGTH: 5 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:16:

TTAGG                                                                                                         5

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:17:

TCCTAGGTCC ATGTCGTACG C                         21

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:18:

TTAGGGTTAG GGTTAGGGTT AGGG                     24

( 2 ) INFORMATION FOR SEQ ID NO:19:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:19:

TGTGAGGGG                                         9

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: other nucleic acid     ( i i i ) HYPOTHETICAL: NO     ( i v ) ANTI-SENSE: NO     ( x i ) SEQUENCE DESCRIPTION: SEQ ID NO:20:

AACGGTGAGG GGCAT                               15

( 2 ) INFORMATION FOR SEQ ID NO:21:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: other nucleic acid ( i i i ) HYPOTHETICAL: NO ( i v ) ANTI-SENSE: NO ( x i ) SEQUENCE DESCRIPTION: SEQ ID NO:21:

TATGCTGTGC CGGGGTCTTC GGGC                                    24